(12) United States Patent  
De Martino et al.

(10) Patent No.: US 7,777,880 B2  
(45) Date of Patent: Aug. 17, 2010

(54) METROLOGICAL CHARACTERISATION OF MICROELECTRONIC CIRCUITS

(75) Inventors: Antonello De Martino, Montrouge (FR); Bernard Drevillon, Clamart (FR)

(73) Assignees: Ecole Polytechnique, Palaiseau (FR); Centre National de la Recherche Scientifique - CNRS, Paris (FR)

( * ) Notice: Subject to any disclaimer, the term of this patent is extended or adjusted under 35 U.S.C. 154(b) by 556 days.

(21) Appl. No.: 11/793,674

(22) PCT Filed: Dec. 22, 2005

(86) PCT No.: PCT/FR2005/051130

§ 371 (c)(1),
(2), (4) Date: Jul. 5, 2007

(87) PCT Pub. No.: WO2006/070161

PCT Pub. Date: Jul. 6, 2006

(65) Prior Publication Data

US 2007/0263219 A1     Nov. 15, 2007

(30) Foreign Application Priority Data

Dec. 24, 2004    (FR)    .................................. 04 53231

(51) Int. Cl.
*G01J 4/00*        (2006.01)

(52) U.S. Cl. ...................................... 356/364; 356/369
(58) Field of Classification Search ......... 356/364–370, 356/625–640; 250/225
See application file for complete search history.

(56) References Cited

U.S. PATENT DOCUMENTS 5,956,145 A     9/1999    Green et al.
6,804,003 B1   10/2004    Wang et al.

FOREIGN PATENT DOCUMENTS

EP        1 411 333 A    4/2004

*Primary Examiner*—Gregory J Toatley, Jr.
*Assistant Examiner*—Tri T Ton
(74) *Attorney, Agent, or Firm*—Young & Thompson

(57) ABSTRACT

Method and a polarimetric measurement device of a planar object carrying patterns repeated regularly and forming the lines of a grid. A first measurement is carried out at zero order, under an angle of incidence $\theta_1$ and for a first azimuthal angle $\phi_1$, a second measurement at least is carried out at zero order, under an angle of incidence $\theta_2$ and for a second azimuthal angle $\phi_2$, the polarization of the incident beam is modulated and the polarization of the reflected beam is analyzed for each measurement, theoretical polarimetric data is calculated for a model object of the real object, the model object including parameters adjustable using a formalism of electromagnetism. An iterative comparison of the measurements is conducted with the theoretical polarimetric data for different values of the adjustable parameters.

23 Claims, 6 Drawing Sheets

METROLOGICAL CHARACTERISATION OF MICROELECTRONIC CIRCUITS

FIELD OF THE INVENTION

The invention relates to a method and a polarimetric measurement device of microelectronic circuits carrying patterns repeated regularly and forming the lines of a grid.

BACKGROUND OF THE INVENTION

The development of the manufacture of microelectronic components implies measurement and control processes and devices which are more and more performing.

Indeed the permanent reduction in the critical dimension of these circuits (CD: Critical Dimension) which is currently 100 nm approx. implies corresponding adaptation of the measurement methods. Simultaneously the increase in size of the wafers and the costs represented by each of them imply the control and the detection of the defects, as soon as possible and, in fact, at each step of the manufacturing process.

To this end, the fact that these wafers carry patterns which are repeated identically is used. The regular repeat of a pattern on a planar support brings about the realisation of an object behaving, from an optical viewpoint, as a grid. The dashes of the grid consist of the sequenced repeat of the pattern.

It is thus that, until now the inventors of this application have used, in laboratory, the Mueller ellipsometry in different spectral domains, for characterising diffraction grids.

More conventionally, the spectroscopic ellipsometry is used in the industry (often under the name "scatterometry") for characterising the circuits. Spectroscopic ellipsometry measurements are then conducted at zero order, that is to say that the beams, respectively, excitation and measurement beams are oriented, relative to the measured object, according to angles bound by the Descartes laws, wherein the plane of incidence is perpendicular to the dashes of the grid formed of the repeat of the pattern.

SUMMARY OF THE INVENTION

The aim of the present invention is to improve these existing measuring methods while increasing their accuracy and while increasing the number and the nature of the elements of the characterised circuits.

To this end, the number of quantities measured relative to the standard "scatterometric" technique may be increased. First of all, polarimetric measurements may be conducted in at least two distinct incidence planes, that is to say while varying the azimuthal angle. Secondly, these measurements may be more complete than conventional ellipsometric measurements. Thus, the determination of the whole Mueller matrix or still of its eigenvalues provides respectively sixteen or four quantities instead of both angles $\Psi$ and $\Delta$ (or equivalent quantities) of standard ellipsometry. In all cases, the more data is acquired, the more it is possible, theoretical, to provide accurate and robust characterisation of the object, but involves a calculation time which may become prohibitive. Consequently, a compromise has to be found between the number of measured data and the possibilities of treatment.

The invention offers therefore a method and a measuring device which while improving significantly the previous measurements is compatible with the data processing methods and means available. More precisely, this method and the apparatus implementing it may be used conveniently in the industry. The processing times requires do not risk penalising the manufacture of the circuits and are compatible with the production rates.

The present invention hence relates to a polarimetric measurement method of a planar object carrying patterns repeated regularly and forming the lines of a grid including the generation of an excitation incident beam on said object forming a measuring beam whereof the orientation relative to the object is represented by an angle of incidence $\theta$ and an azimuthal angle $\phi$.

According to the invention,
a first measuring is carried out at zero order, under an angle of incidence $\theta_1$ and for a first azimuthal angle $\phi_1$,
a second measurement at least is carried out at zero order, under an angle of incidence $\theta_2$ and for a second azimuthal angle $\phi_2$,
the polarisation of the incident beam is modulated and the polarisation of the reflected beam is analysed for each measurement so as to obtain experimental polarimetric data,
theoretical polarimetric data is calculated for a model object of the real object, the model object including parameters adjustable using a formalism of electromagnetism,
the object is characterised by conducting an iterative comparison of the measurements with the theoretical polarimetric data for different values of the adjustable parameters.

In different particular embodiments of the invention each exhibiting their specific advantages:
the theoretical polarimetric data and the measurements are each represented by a complete Mueller matrix,
the theoretical polarimetric data and the measurements are obtained from a linear combination of the eigenvalues of the complete Mueller matrix,
the azimuthal angles $\phi_1$ and $\phi_2$ are comprised between 30° and 90°, advantageously between 30° and 60° relative to the repeat direction of the patterns,
the polarimetric measurements are obtained in relation to the wavelength so as to obtain spectroscopic measurements,
the spectral range of the wavelength is situated in the near ultraviolet,
the spectral range of the wavelength is situated in the visible,
the iterative comparison is a method of the least square type,
the calculation of the theoretical polarimetric data uses a method of the Weidner model type for the grids with asymmetrical profile.

The invention also relates to a device for the implementation of the polarimetric measurement method.

According to a first embodiment of the invention the device includes two Mueller polarimeters including a light source, two polarimeters each including a polarisation state generator (PSG), a polarisation state analyser (PSA) and a detector.

According to the invention, the azimuthal orientation of one differs from that of the other and the points measured on the object, by one and the other, are superimposed.

According to a second embodiment of the invention, the device includes a light source for the excitation of an object, a polarisation state generator (PSG), optical means capable of directing an excitation luminous flux generated by the source towards the object, a polarisation state analyser (PSA), a detector capable of receiving a measurement luminous flux generated by the object in response to the excitation flux, measuring optical means, collecting the measurement luminous flux generated by the object and directing it towards the detector.

According to the invention, the second device includes means enabling the detector to generate distinct measurements according to the azimuthal angle of the excitation luminous flux on the object and to the polarisation of the reflected luminous flux.

In different particular embodiments of the invention each exhibiting their specific advantages:
- the device includes optical means such as the excitation light beam, at the object, exhibits a weak spatial coherence ranging between 5 and 100 times the diffraction limit of the source,
- the light source is a filtered conventional source,
- the light source includes one or several lasers of different wavelengths,
- the device includes a semi-transparent blade enabling to separate the luminous fluxes, respectively excitation and measurement fluxes,
- the device includes a wide digital aperture objective, having a Fourier plane, capable of being travelled by the excitation flux and of making it converge on the object and also capable of collecting the measurement flux generated by the object,
- the optical excitation means include a mask, in an optically conjugated plane of the Fourier plane of the objective, capable of generating excitation luminous flux incident on the object according to differentiated azimuthal angles,
- the optical measuring means include a mask, in an optically conjugated plane of the Fourier plane of the objective, capable of collecting the measurement luminous fluxes emitted by the object according to differentiated azimuthal angles,
- the detector is a multipoint detector, placed in an optically conjugated plane of the Fourier plane of the objective and, capable of measuring simultaneously the measurement luminous fluxes emitted by the object according to differentiated azimuthal angles,
- the PSG and the PSA include means for modulating the polarisation of the incident beam and means for analysing the polarisation of the reflected beam, so as to measure the whole Mueller matrix of the grid,
- the device includes means for conducting polarimetric measurements in relation to the wavelength so as to obtain spectroscopic measurements,
- the spectral range of the wavelength is situated in the near ultraviolet,
- the spectral range of the wavelength is situated in the visible.

BRIEF DESCRIPTION OF THE DRAWINGS

An embodiment of the invention will be described in more detail with reference to the appended drawings wherein.

DETAILED DESCRIPTION OF EMBODIMENTS

Figure 1:
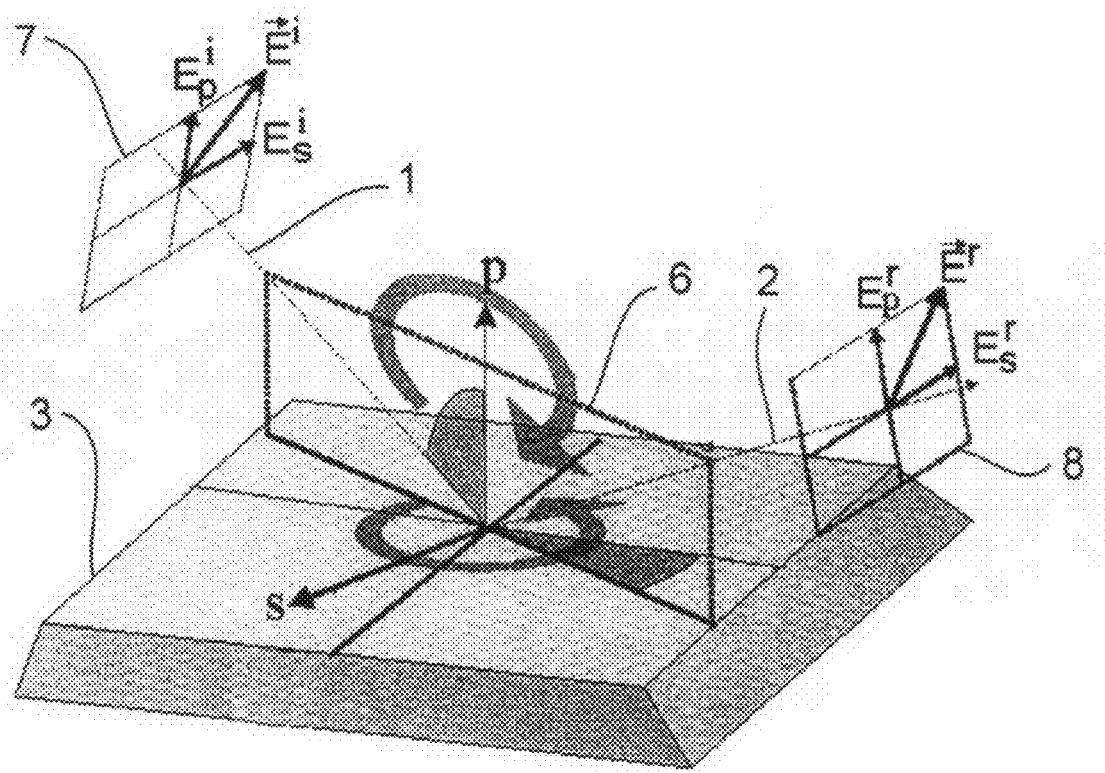
FIG. 1 is a diagrammatic representation of a polarimetric measurement system, while showing the main significant parameters.

On FIG. 1, a planar object 3 receives the excitation beam 1 and returns the measuring beam 2. This excitation beam 1 is oriented relative to the object 3 under an angle of incidence $\theta$. The plane of incidence 6 is oriented under the azimuthal angle $\phi$. The point of interest here is the zero order, this is to say that, as stated above, the beams, respectively, excitation 1 and measurement 2 beams are oriented, relative to the measured object 3, according to angles bound by the Descartes laws. The polarisation parameters of the incidence 1 and measuring 2 beams are respectively represented on the marks 7 and 8. The polarisation vectors, respectively $E^i$ and $E^r$ incident and reflected, are broken down on axes orthogonal at $E^i_p$ $E^i_s$ and $E^r_p$ $E^r_s$.

Figure 2:
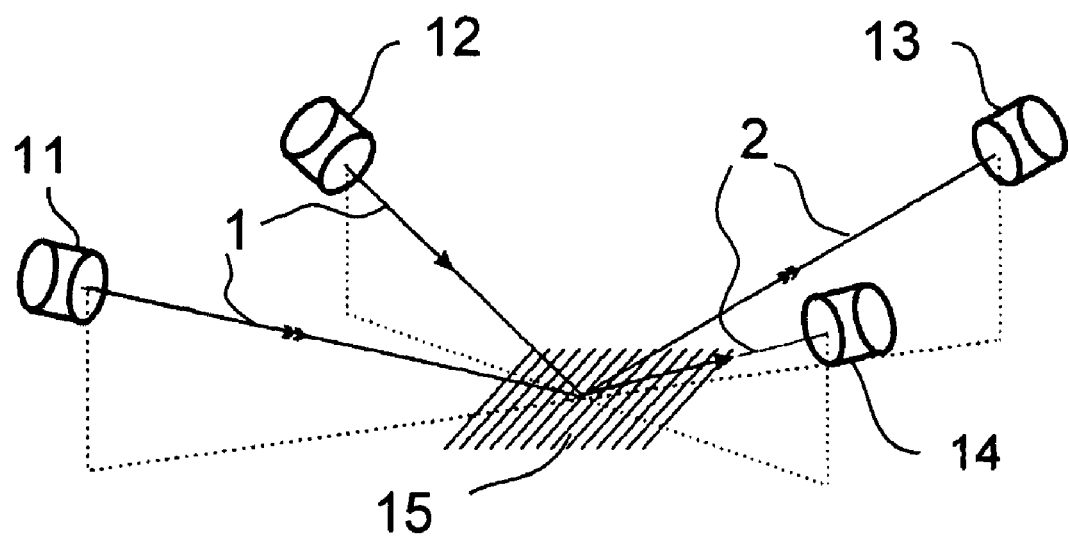
FIG. 2 is a diagrammatic representation of a device of the invention according to a first embodiment.

FIG. 2 is a diagrammatic representation of a first embodiment of the invention. The object 15 carries patterns which are represented diagrammatically by the direction of their repeat. Two Mueller polarimeters are represented diagrammatically by their respective polarisation state generators (PSG) 11 and 12 and by their respective polarisation state analysers (PSA) 13 and 14. For simplification purposes, the light sources and the detectors have not been represented. An excitation incident beam 1 is generated on the object forming a measuring beam whereof the orientation relative to the object is represented by an angle of incidence $\theta$ and an azimuthal angle $\phi$.

According to the invention, when measuring, the following measurements are made, with one of the polarimeters, a first measurement is carried out at zero order, under an angle of incidence $\theta_1$ and under a first azimuthal angle $\phi_1$ so as to obtain the corresponding polarimetric data.

The following measurements are made simultaneously, with the other one of the polarimeters, at least one a second measurement at least is carried out at zero order, under an angle of incidence $\theta_2$ and under a second azimuthal angle $\phi_2$ so as to obtain the corresponding polarimetric data.

The PSG 11, 12 and the PSA 13, 14 include means for modulating the polarisation of the incident beam 1 and means for analysing the polarisation of the reflected beam 2, so as to measure simultaneously the entirety of both Mueller matrices that is to say 16 polarimetric data per matrix, at different azimuthal angles $\phi_1$ and $\phi_2$.

The polarimeters have been adjusted so that the points measured on the object 15, by one and the other, are superimposed accurately.

These measurements may be performed at different wavelengths, over a domain extending typically on the visible and/or the ultraviolet up to approx. 200 nm.

Figure 3:
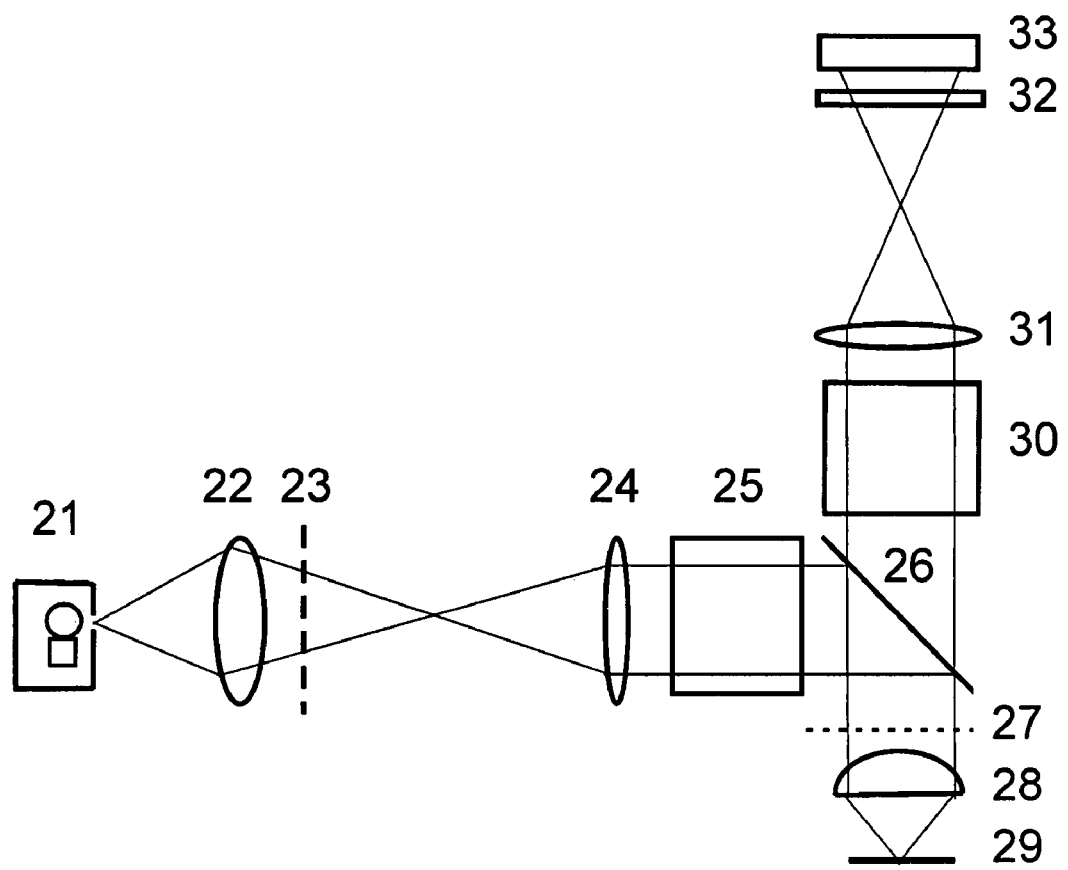
FIG. 3 is a diagrammatic representation of a device of the invention according to a second embodiment.
Figure 4:
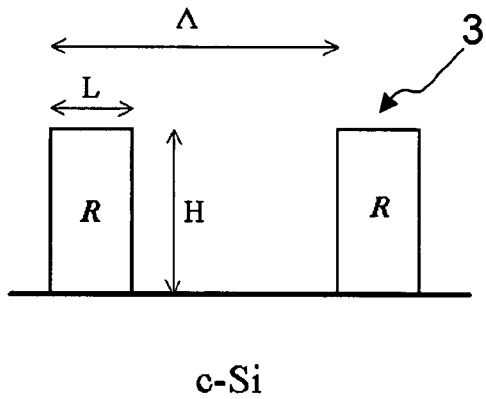
FIGS. 4 and 5 represent, as sectional views, two types of geometric models, one on FIG. 4 has straight-flanked dashes, the other on FIG. 5 has dashes with tilted flanks.
Figure 5:
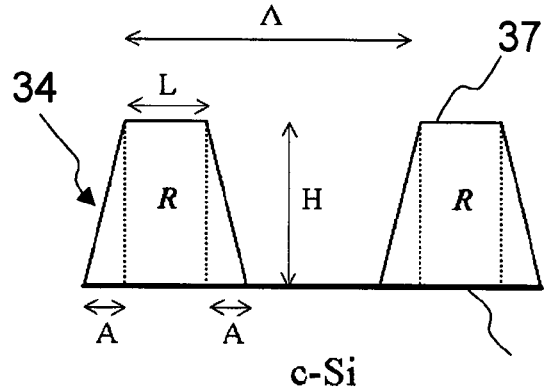

FIG. 3 represents another embodiment of the invention operating in the visible implementing an angular resolution Muller polarimeter. It includes a polarisation state generator (PSG) 25 acting on the parallel luminous flux generated by the source 21, the lens 22, the mask 23 and the lens 24 and a polarisation state analyser (PSA) 30 acting on the parallel luminous flux by a wide digital aperture objective, advantageously greater than 0.95, of the microscope objective 28 type received from the object 29. The wide digital aperture enables to obtain wide angle sweep at the detector.

The device according to this second embodiment includes optical means so that the excitation light beam, at the object, exhibits a weak spatial coherence ranging between 5 and 100 times the diffraction limit of the source 21. The source 21 may be formed of a conventional filtered white source or of one or several lasers of different wavelengths with small coherence, the purpose being to illuminate as many dashes as possible.

A semi-transparent blade 26 enabling to separate the luminous fluxes, respectively excitation and measurement fluxes. The lens 31, directs the luminous flux exiting the PSA towards the multipoint receiver 33 through the filter 32.

The PSG 25 is formed of a linear polariser and of two liquid crystals (LC), ferroelectric or nematic. A quarter wave blade can be inserted between both LC in order to improve the performances of the apparatus. The PSA 30 is formed, symmetrically, of two LC and of a linear polariser (or analyser). The orientation and the phase shifts of each of the LC (identical for the PSG and the PSA) correspond to optimised values. The multipoint receiver 33 is a CCD camera, coupled to a monochromator. The complete measurement of the Mueller matrix (sixteenth coefficients instead of two in conventional ellipsometry) is obtained from sixteenth measurements, while applying consecutively two phase shift values to the liquid crystals, whereof the orientation is fixed. Taking the switching times of the CL into account, this spectroscopic measurement, in the visible domain, is performed within one second approximately.

For an operation in the ultraviolet, a spectral domain where the liquid crystals are opaque, a PSG consisting of a polariser and of a retardation plate adapted to the operating wavelength of the objective may be used, and which may be situated at least at four different orientations by rotation in its plane. The PSA is formed of the same elements, travelled in reverse direction. The objective may be either a mirror objective, whereof the advantage is achromaticity, or an objective used for the UV lithography, provided for a given wavelength (typically 248 nm), wherein the advantage is then better transmission and a greater digital aperture with respect to the typical values of the mirror objectives.

The conical diffraction consists in conducting measurements with different azimuthal angles. Used jointly, the Mueller polarimetry exhibits numerous advantages relative to the conventional scatterometry. Indeed the Mueller polarimetry brings about greater accuracy on the determination of certain parameters of the grids (for instance in the case of trapezoid dashes). Moreover, it enables to solve certain ambiguities inherent to conventional scatterometry, for instance in the case of superimposed structures (so-called "overlay" in microelectronics).

Regardless of the embodiment, the theoretical polarimetric data is calculated in parallel for a model object of the real object. The model object includes parameters adjustable using a formalism of electromagnetism.

The theoretical polarimetric data and the measurements are each either represented by a complete Mueller matrix, or a linear combination of its eigenvalues.

The operating mode, simplified, for obtaining the eigenvalues of the Mueller matrix is described below. This operating mode provides the 4 eigenvalues of the matrix $M M_0^{-1}$, where M is the Mueller matrix of the object to be characterised and $M_0$ the Mueller matrix assumed as well-known and non singular, of a reference object. This operating mode hence forms an intermediate between conventional ellipsometry, which only provides two magnitudes, and the complete Mueller polarimetry, which provides the 16 elements of the matrix.

The main interest of this operating mode is its easy implementation, since it does not require any complete calibration of the polarimeter(s). One proceeds as follows:

firstly, the reference matrix $B_0 = A M_0 W$ of the reference object of Mueller matrix $M_0$ is measured, (such object may be silicon for instance, optionally with an oxide layer of known thickness, or glass), for the object to be characterised, the matrix is measured B=AMW, and the following products are formed:

$$B_0^{-1} B = W^{-1} M_0^{-1} M W \text{ and } B B_0^{-1} = A M M_0^{-1} A^{-1}$$

These matrix products have the same eigenvalues as $M_0^{-1} M$ and $M M_0^{-1}$, which can hence be determined without knowing neither A, nor W. These eigenvalues being theoretically the same for both products, a simple test of accuracy of the measurements is available. Besides, $M_0$ being assumed as known, any theoretical model used for reconstructing the forms of the dashes of the grid from the matrix M can be used just as well, with hardly longer calculation time, with the eigenvalues of $M M_0^{-1}$.

The object is then characterised by conducting an iterative comparison of the measurements with the theoretical polarimetric data for different values of the adjustable parameters.

The optimum values of the parameters of the model object are determined by an iterative method of the least square type, as for example the method of the $\chi^2$.

The calculation may also use a method of the Weidner model type for the grids with asymmetrical profile.

The advantages according to the invention are illustrated below by two examples.

The first of these examples, represented on FIGS. 4 to 7, shows the possibility of measuring accurately the forms of the section of the dashes and more particularly of distinguishing the most suitable model between the model 34 with dashes having tilted flanks and the model 35 with dashes having straight flanks for a single object.

The results obtained with a Mueller spectroscopic polarimeter operating in the visible (450-750 nm) under several azimuthal angles have been compared with the results obtained by conventional ellipsometry under a single angle ($\phi=0°$) in a greater spectral domain (250-800 nm).

L is the width of the dash, H its height and, in the case of the objects 34 with tilted flanks, A is the semi-difference between the width of the dash at its base 36 and at its apex 37. The period of the grid is ^.

The rated values of these parameters are:

^=240 nm,

H=230 nm,

L=70 nm,

A=0 nm.

These values are taken as a starting point for calculation by the least square method ($\chi^2$) which is calculated while conducting a series of measurements:

relating to N ellipsometric magnitudes $Y_i$, where the index varies from 1 to N (for instance, in the case of conventional ellipsometry $Y_1=\Psi$, $Y_2=\Delta$ and hence N=2; whereas in Mueller polarimetry N=16 since the $Y_i$ are the 16 elements of the complete matrix), over a set of M wavelengths $\lambda_j$, ($1 \leq j \leq M$), over a set of P values of the polar $\theta_k$ and azimuthal $\phi_k$ angles ($1 \leq k \leq P$) and the experimental values of $Y_i$ are adjusted, that is to say $Y_i^{exp}(\lambda_j, \theta_k, \phi_k)$ by a model providing theoretical values $Y_i^{th}$ of these same magnitudes $Y_i$.

The $X^2$ corresponding to this set of measurements and of simulations is written as follows:

$$\chi^2 = \frac{1}{NMP} \sum_{i,j,k} (Y_i^{exp}(\lambda_j, \theta_k, \phi_k) - Y_i^{th}(\lambda_j, \theta_k, \phi_k))^2$$

Figure 6:
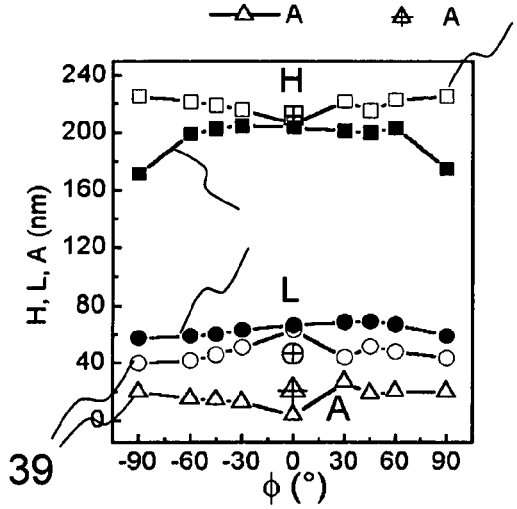
FIGS. 6 to 9 represent the comparative results of the measurements obtained with the models of FIGS. 4 and 5.

FIG. 6 represents the values of parameters obtained for one and the other of the models, with straight dashes 35 and with tilted dashes 34, by a conventional ellipsometry measurement and by Mueller polarimetry for different azimuthal angles $\phi$. The parameters in nm are represented in relation to of the azimuthal angle $\phi$. The Mueller polarimetry enables of distinguishing the most suitable model. The curves 38 and 39 of both models are clearly distinct. Ideally, the curves should be independent of $\phi$. It is the curve 39 corresponding to the model with tilted dashes 34 which exhibits the least dependence.

Figure 7:
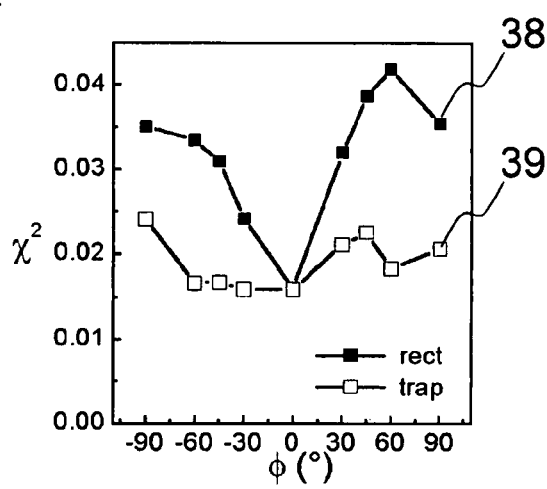

FIG. 7 represents the values of the $\chi^2$ obtained by Mueller polarimetry for both models. The variations of the $\chi^2$ in relation to the azimuthal angle $\phi$ enable of distinguishing the most suitable model. The $\chi^2$ that is to say the difference between the measured values and the simulated values is the smallest for the model with tilted dashes 34, represented by the curve 39, which is consequently the most suitable model.

This allows thus to check that the method according to the invention enables net determination of the most suitable model, which is not accessible by the conventional measurement.

Figures 8, 9:
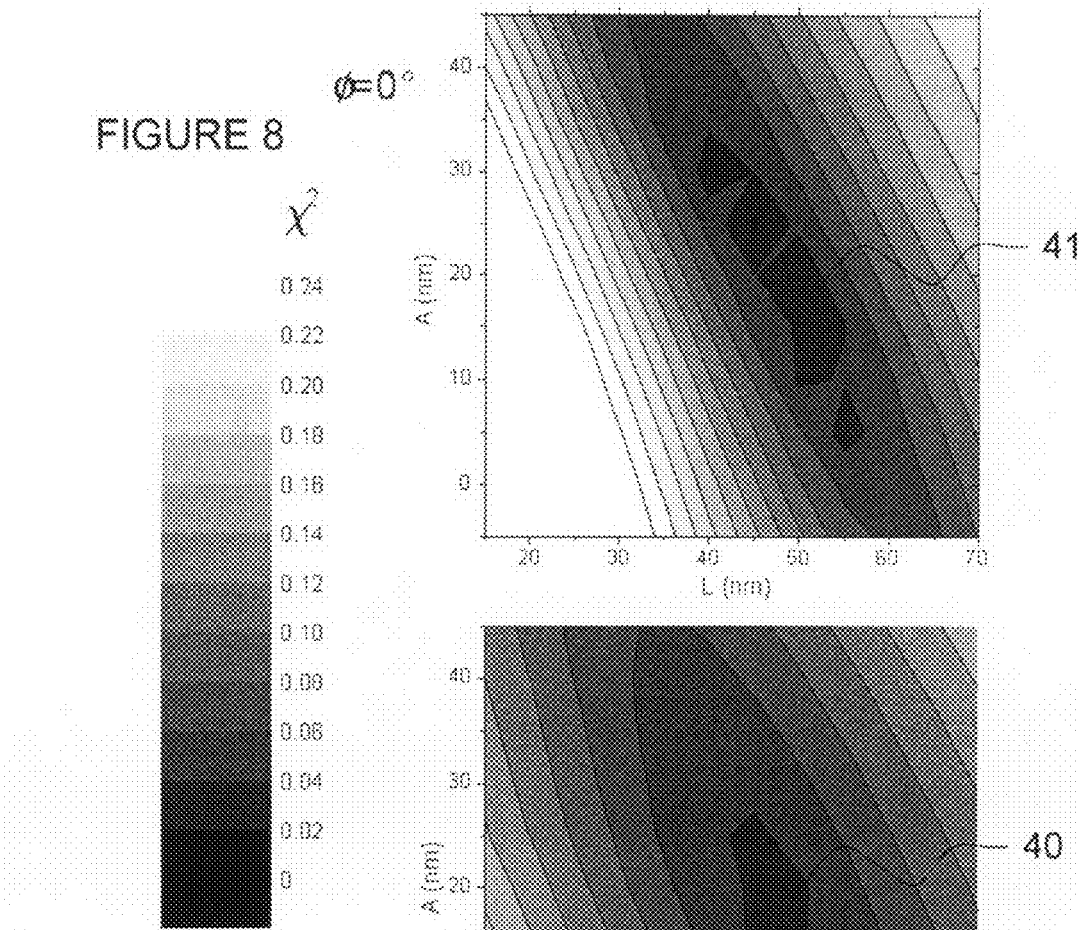
Figure 10:
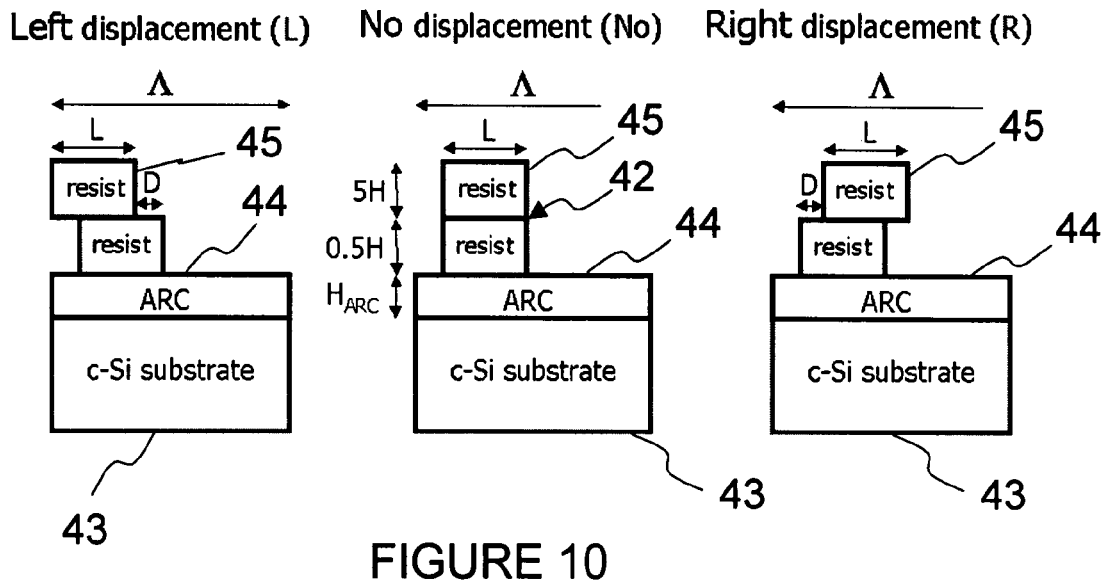
FIG. 10 represents the different types of overlay useful to be measured.
Figure 11:
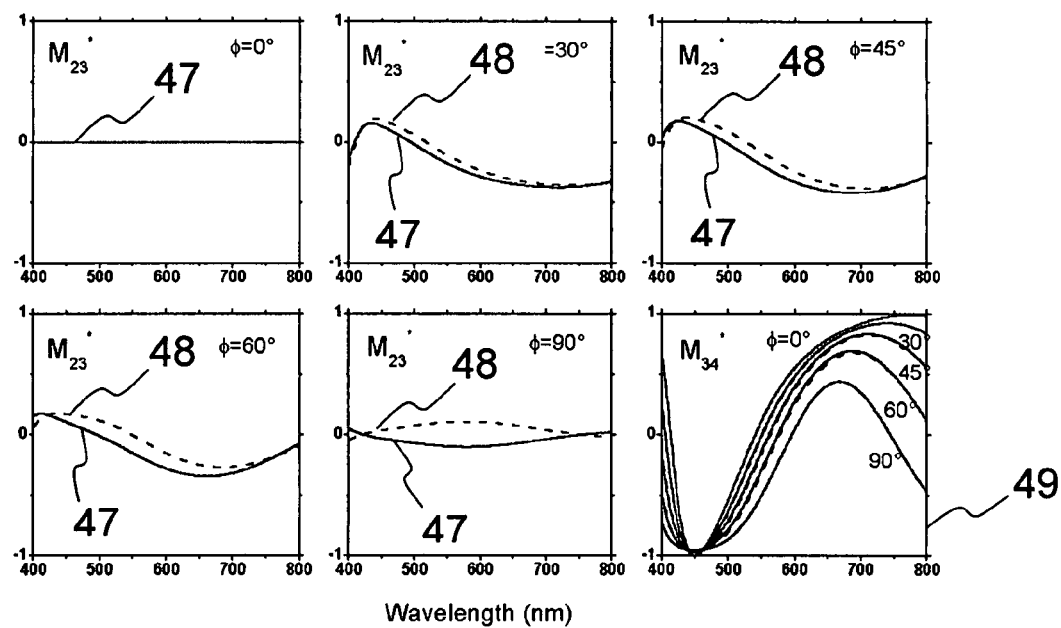
FIG. 11 represents the results obtained on different parameters of the Mueller matrix when measuring the objects of FIG. 10.

FIGS. 8 and 9 are representations of the parameter $\chi^2$ in relation to the parameters A and L compared with the measurements taken at an azimuthal angle $\phi=0°$ (FIG. 8) and with the average of the measurements taken at $\phi=30°$ and $\phi=60°$ in Mueller polarimetry (FIG. 9). It appears thus, as expected with two measurements under the angles of 30° and 60° the convergence 40 is obtained without any possible ambiguity whereas with the single measurement at 0°, the point of convergence 41 is uncertain and hence does not enable an accurate measurement.

It is thus confirmed that the measurements under the angles of 30° and 60° enable to waive the uncertainty.

The measurements should then be conducted under angles ranging between 30° and 60°, without excluding any measurement up to an angle of 90°.

The second example consists of the measurement of an overlay of the layers relative to one another, in a stack. Such an overlay, in one direction or the other is represented diagrammatically on FIG. 12 relative to a perfect stack 42, without any overlay represented in the centre.

The parameters defining this stack are the width of the dash L, the total height of the stack H and the overlay D. The period of the grid is $\hat{}$.

The model suggested by Weidner et al is used (Proc SPIE, 5375 (2004)). A silicon Si substrate 43 is covered with an antiglare layer 44 (ARC) of thickness 90 nm. On this layer, a resin layer 45 is deposited forming a grid of pitch $\hat{}$=145 nm. The grid obtained is more accurately formed of two grids of same dimension L=58 nm (i.e. $\hat{}/4$), of same height 0.5 H=50 nm, and exhibiting an overlay D=14.5 nm (i.e. L/4).

The simulations according to the model of Weidner et al on FIG. 13 reveal results for displacements to the right (R) and to the left (L) for two standardised elements of the matrix: $M_{23}*=M_{23}/M_{11}$ and $M_{34}*=M_{34}/M_{11}$. The element $M_{23}*$ is obtained only from measurements by Mueller polarimetry whereas the element $M_{34}*$ is given by the Mueller polarimetry and standard ellipsometry. The curve in full line 47 and the curve in dotted line 48 correspond respectively to the displacements to the right (R) and to the left (L). These curves are represented according to the wave number (nm) and for different azimuthal angles.

The representation 49 of the element $M_{34}*$ according to the wave number for azimuthal angles $\phi$ varying from 0° to 90° shows that the model of Weidner et al does not produce any significant difference in the direction of the overlay regardless of the angle $\phi$. The curves obtained for displacements to the right 47 and to the left 48 are practically superimposed. Conversely, the parameter $M_{23}*$, which is only valid in Mueller polarisation, enables a significant distinction between the displacements to the right or to the left except for $\phi=0°$, but with the greatest sensitivity for $\phi=90°$.

Regardless of the calculation method used, the Mueller polarimetry according to the invention, including measurements under several azimuthal angles enables to obtain a larger number of parameters, which implies more accurate and more complete characterisation of an object.

The invention claimed is:

1. A polarimetric measurement method of a planar object carrying regularly repeated patterns and forming lines of a grid including generation of an excitation incident beam on said object forming a measuring beam whereof the orientation relative to the object is represented by an angle of incidence $\theta$ and an azimuthal angle $\phi$, said method comprising:
    carrying out a first measuring at zero order, under an angle of incidence $\theta_1$ and for a first azimuthal angle $\phi_1$,
    carrying out a second measurement at least at zero order, under an angle of incidence $\theta_2$ and for a second azimuthal angle $\phi_2$,
    modulating the polarisation of the incident beam and analyzing the polarisation of the reflected beam for each measurement so as to obtain experimental polarimetric data,
    calculating theoretical polarimetric data for a model object of the real object, said model object including parameters adjustable using a formalism of electromagnetism,
    conducting an iterative comparison of the measurements with the theoretical polarimetric data for different values of the adjustable parameters to characterize the object.

2. The polarimetric measurement method according to claim 1, wherein the theoretical polarimetric data and the measurements are each represented by a complete Mueller matrix.

3. The polarimetric measurement method according to claim 2, wherein the theoretical polarimetric data and the measurements are obtained from a linear combination of the eigenvalues of the complete Mueller matrix.

4. The polarimetric measurement method according to claim 1, wherein the azimuthal angles $\phi_1$ and $\phi_2$ are comprised between 30° and 90° relative to the repeat direction of the patterns.

5. The polarimetric measurement method according to claim 1, wherein the polarimetric measurements are obtained in relation to the wavelength so as to obtain spectroscopic measurements.

6. The polarimetric measurement method according to claim 5, wherein the spectral range of the wavelength is situated in the near ultraviolet.

7. The polarimetric measurement method according to claim 5, wherein the spectral range of the wavelength is situated in the visible.

8. The polarimetric measurement method according to claim 1, wherein the iterative comparison is a method of the least square type.

9. The polarimetric measurement method according to claim 1, wherein the calculation of the theoretical polarimetric data uses a method of the Weidner model type for the grids with asymmetrical profile.

10. A device for the implementation of the polarimetric measurement method according to claim 1, including a light source, two polarimeters each including a polarisation state generator (PSG) (11, 12), a polarisation state analyser (PSA) (13, 14) and a detector, wherein:
- the azimuthal orientation of one $\phi_1$ differs from that of the other $\phi_2$,
- the points measured on the object, by one and the other, are superimposed.

11. A device for the implementation of the polarimetric measurement method according to claim 1, including a light source (21) for the excitation of an object (29), a polarisation state generator (PSG) (25), optical means capable of directing an excitation luminous flux generated by the source (21) towards the object (29), a polarisation state analyser (PSA) (30), a detector (33) capable of receiving a measurement luminous flux generated by the object (29) in response to the excitation flux, measuring optical means, collecting the measurement luminous flux generated by the object (29) and directing the measurement luminous flux towards the detector (33), and further including means enabling the detector to generate distinct measurements according to the azimuthal angle of the excitation luminous flux on the object (29) and the polarisation of the reflected luminous flux.

12. A device for the implementation of the polarimetric measurement method according to claim 11, wherein the optical means is an excitation light beam, at the object, that exhibits a weak spatial coherence ranging between 5 and 100 times the diffraction limit of the source (21).

13. A device for the implementation of the polarimetric measurement method according to claim 12, wherein the light source (21) is a filtered conventional source.

14. A device for the implementation of the polarimetric measurement method according to claim 12, wherein the light source (21) includes one or several lasers of different wavelengths.

15. A device for the implementation of the polarimetric measurement method according to claim 11, further including a semi-transparent blade (26) enabling to separate the luminous fluxes, respectively excitation and measurement fluxes.

16. A device for the implementation of the polarimetric measurement method according to claim 11, further including a wide digital aperture objective, having a Fourier plane, capable of being travelled by the excitation flux and of making the excitation flux converge on the object (29) and also capable of collecting the measurement flux generated by the object (29).

17. A device for the implementation of the polarimetric measurement method according to claim 11, wherein the optical excitation means include a mask, in an optically conjugated plane of the Fourier plane of the objective, capable of generating excitation luminous fluxes incident on the object (29) according to differentiated azimuthal angles.

18. A device for the implementation of the polarimetric measurement method according to claim 11, wherein the optical measuring means include a mask, in an optically conjugated plane of the Fourier plane of the objective, capable of collecting the measurement luminous fluxes emitted by the object (29) according to differentiated azimuthal angles.

19. A device for the implementation of the polarimetric measurement method according to claim 11, wherein the detector is a multipoint detector, placed in an optically conjugated plane of the Fourier plane of the objective and, capable of measuring simultaneously measurement luminous fluxes emitted by the object (29) according to differentiated azimuthal angles.

20. A device for the implementation of the polarimetric measurement method according to claim 10, wherein the PSG (25) and the PSA (30) include means for modulating the polarisation of the incident beam and means for analysing the polarisation of the reflected beam, so as to measure the whole Mueller matrix of the grid.

21. A device for the implementation of the polarimetric measurement method according to claim 10, further including means for conducting polarimetric measurements in relation to the wavelength so as to obtain spectroscopic measurements.

22. A device for the implementation of the polarimetric measurement method according to claim 21, wherein the spectral range of the wavelength is situated in the near ultraviolet.

23. A device for the implementation of the polarimetric measurement method according to claim 21, wherein the spectral range of the wavelength is situated in the visible.

* * * * *